United States Patent
Kim et al.

(10) Patent No.: US 9,934,426 B2
(45) Date of Patent: Apr. 3, 2018

(54) SYSTEM AND METHOD FOR INSPECTING EMOTION RECOGNITION CAPABILITY USING MULTISENSORY INFORMATION, AND SYSTEM AND METHOD FOR TRAINING EMOTION RECOGNITION USING MULTISENSORY INFORMATION

(71) Applicant: KOREA UNIVERSITY RESEARCH AND BUSINESS FOUNDATION, Seoul (KR)

(72) Inventors: Hyun Teak Kim, Seoul (KR); Ji Woon Jeong, Seoul (KR); Jiyoung Kim, Seoul (KR); Yeseul Chun, Seoul (KR)

(73) Assignee: KOREA UNIVERSITY RESEARCH AND BUSINESS FOUNDATION, Seoul (KR)

( * ) Notice: Subject to any disclaimer, the term of this patent is extended or adjusted under 35 U.S.C. 154(b) by 0 days.

(21) Appl. No.: 15/024,453

(22) PCT Filed: Sep. 26, 2014

(86) PCT No.: PCT/KR2014/009010
§ 371 (c)(1),
(2) Date: Mar. 24, 2016

(87) PCT Pub. No.: WO2015/046945
PCT Pub. Date: Apr. 2, 2015

(65) Prior Publication Data
US 2016/0217322 A1    Jul. 28, 2016

(30) Foreign Application Priority Data
Sep. 27, 2013 (KR) .................. 10-2013-0115385

(51) Int. Cl.
*G06K 9/00* (2006.01)
*G06F 19/00* (2018.01)
(Continued)

(52) U.S. Cl.
CPC ....... *G06K 9/00308* (2013.01); *G06F 19/345* (2013.01); *G06K 9/00* (2013.01);
(Continued)

(58) Field of Classification Search
CPC ....... A61B 5/16; A61B 5/165; A61B 2503/12; A61B 5/0245; A61B 5/08; A61B 5/11;
(Continued)

(56) References Cited

U.S. PATENT DOCUMENTS

| 5,647,834 A * | 7/1997 | Ron ................. A61B 5/16 600/23 |
| 7,955,259 B2 * | 6/2011 | Lee ................. A61M 21/00 128/905 |

(Continued)

FOREIGN PATENT DOCUMENTS

| CA | 2754835 | 4/2013 |
| KR | 1020030029660 | 4/2003 |

(Continued)

*Primary Examiner* — Aklilu Woldemariam
(74) *Attorney, Agent, or Firm* — Duane Morris LLP; J. Rodman Steele, Jr.; Gregory M. Lefkowitz

(57) ABSTRACT

The present invention relates to a system and a method for inspecting an emotion recognition capability using multisensory information, and a system and a method for training emotion recognition using multisensory information. More particularly, the present invention comprises: an output unit for outputting multisensory information including at least one emotional state of a subject person to the outside; an input unit for receiving, from a tested person, emotional state information, which indicates whether the output multisensory information is identical to at least one emotional state of the subject person, on the basis of the output multisensory information; a comparison identification unit for identifying whether the received emotional state information is identical to reference emotional state information corresponding to the multisensory information pre-stored in
(Continued)

a storage unit; and a control unit for determining an emotion recognition capability of the tested person according to a result of the identification of the received emotional state information. Due to such a configuration, a system and a method for inspecting an emotion recognition capability using multisensory information and a system and a method for training emotion recognition using multisensory information according to the present invention can determine an emotional state of a subject person by using multisensory information and thus can easily identify an emotion recognition capability of other people.

11 Claims, 6 Drawing Sheets

(51) Int. Cl.
*G06K 9/66* (2006.01)
*G10L 15/06* (2013.01)
*G10L 25/63* (2013.01)

(52) U.S. Cl.
CPC ............. *G06K 9/66* (2013.01); *G10L 15/063* (2013.01); *G10L 25/63* (2013.01)

(58) Field of Classification Search
CPC .. G06F 19/363; G06F 17/30244; G06F 3/005; G06F 3/011; G06F 3/017; G06F 3/016; G06F 3/167; G06F 19/3481; G06F 2203/011; G06F 17/3053; G06F 21/6245; G06N 3/004; G06N 3/006; G09B 23/28; G09B 21/008; G06Q 30/02; G06K 9/00315; G06K 9/00335; G06K 9/00288; G06K 9/66; G06K 9/00577; G06K 9/4647; G06K 9/00214; G06K 9/00664; H04M 1/0264; H04N 2201/3225; H04N 5/23219; H04W 4/16; A63F 13/56; A63F 13/57; A63F 13/577; G02B 2027/0138; G02B 2027/014; G06T 13/80; G06T 15/10; G06T 7/60; G06T 2200/04; G06T 2215/16; A63J 2005/008; G10L 19/00; G10L 17/26; G10L 25/48; G10L 25/90; A61M 2021/0044; A61M 21/00; G05B 19/42; G05B 2219/40391; G05B 2219/40395; B25J 19/02; Y10S 901/01; Y10S 901/03
USPC ........ 382/103, 118, 155, 159, 190; 600/301, 600/500
See application file for complete search history.

(56) References Cited

U.S. PATENT DOCUMENTS

| | | | | |
|---|---|---|---|---|
| 8,321,221 | B2* | 11/2012 | Aoyama | G10L 15/22 318/567 |
| 8,401,248 | B1* | 3/2013 | Moon | G06Q 30/0242 382/103 |
| 8,798,374 | B2* | 8/2014 | Bartlett | G06K 9/00335 382/118 |
| 2005/0283055 | A1* | 12/2005 | Shirai | A61B 5/16 600/301 |
| 2009/0163777 | A1* | 6/2009 | Jung | A61B 5/04842 600/301 |
| 2009/0285456 | A1* | 11/2009 | Moon | G06K 9/00335 382/118 |
| 2010/0010371 | A1* | 1/2010 | Zayfert | A61B 5/16 600/558 |
| 2011/0027764 | A1 | 2/2011 | Bianchi-Demichell et al. | |
| 2012/0035428 | A1 | 2/2012 | Roberts et al. | |
| 2012/0116186 | A1* | 5/2012 | Shrivastav | A61B 5/0507 600/301 |
| 2013/0211277 | A1* | 8/2013 | Berg | A61M 21/0094 600/547 |
| 2014/0003652 | A1* | 1/2014 | Fedorovskaya | G06F 17/30286 382/103 |
| 2014/0095189 | A1* | 4/2014 | Holmes | G06F 19/363 705/2 |
| 2014/0112556 | A1* | 4/2014 | Kalinli-Akbacak | G10L 25/63 382/128 |
| 2014/0303450 | A1* | 10/2014 | Caponi | A61B 5/165 600/301 |
| 2014/0347265 | A1* | 11/2014 | Aimone | G09G 3/003 345/156 |
| 2015/0048178 | A1* | 2/2015 | Edwards | A61L 9/032 239/13 |
| 2015/0290795 | A1* | 10/2015 | Oleynik | G05B 19/42 700/257 |
| 2015/0301592 | A1* | 10/2015 | Miller | G06F 3/011 345/156 |
| 2015/0339363 | A1* | 11/2015 | Moldoveanu | A61B 5/165 707/723 |
| 2016/0059412 | A1* | 3/2016 | Oleynik | B25J 9/163 700/257 |

FOREIGN PATENT DOCUMENTS

| | | |
|---|---|---|
| KR | 1007490320000 | 8/2007 |
| KR | 1009861090000 | 10/2010 |
| KR | 1011823480000 | 9/2012 |

* cited by examiner

FIG. 4

| Visual stimulus (face) | Auditory stimulus (voice) | Correct answer reaction |
|---|---|---|
| Happy | Happy | Same |
| Angry | Angry | |
| Happy | Angry | Different |
| Angry | Happy | |

Test scores before and after training
and generalization test scores (a)

Scores vs number of training cycles (b)

SYSTEM AND METHOD FOR INSPECTING EMOTION RECOGNITION CAPABILITY USING MULTISENSORY INFORMATION, AND SYSTEM AND METHOD FOR TRAINING EMOTION RECOGNITION USING MULTISENSORY INFORMATION

CROSS-REFERENCE TO RELATED APPLICATIONS

This application is a § 371 national stage entry of International Application No. PCT/KR2014/009010, filed on Sep. 26, 2014, which claims priority to South Korean Patent Application No. 10-2013-0115385, filed on Sep. 27, 2013, the entire contents of which are incorporated herein by reference.

TECHNICAL FIELD

The present disclosure relates to a system and method for inspecting an emotion recognition capability using multisensory information and a system and method for training emotion recognition using multisensory information, and more particularly, to a system and method for inspecting an emotion recognition capability using multisensory information and a system and method for training emotion recognition using multisensory information that allows for easy recognition of a current emotional state of other person by using multiple sensory information.

BACKGROUND ART

To build and maintain good relationships with others in life, it is important to accurately perceive and interpret feelings or emotions in others involved in relationships. It is referred to as emotion recognition.

For example, emotion recognition refers to the abilities to recognize whether others are feeling a happy or sad emotion from faces, or recognize whether others are feeling a peaceful or angry emotion from voices.

Emotion recognition is a very difficult aspect in the interpersonal relationships to beginners having just taken their first steps into the society or individuals with relatively low social skills. Particularly, patients who look like seemingly normal people, for example, patients with schizophrenia (dissociative identity disorder), autism, and depression have difficulties in recognizing others' emotional states and responding thereto.

As described in the foregoing, a description of a system and method for inspecting an emotion recognition capability using multisensory information and a system and method for training emotion recognition using multisensory information is provided as below.

Prior Art 1 Korean Patent Publication No. 2012-0068135 (Jun. 27, 2012) relates to a similar auditory learning method using sound wave analysis.

Prior Art 1 includes a sound transmission step S110 at which a normal person hears a sound from a speaker 110, an emotion recording step S120 at which a feeling storage means 120 receives an input of an emotion the normal person feels in response to the sound and records it, a similar auditory conversion step S130 at which a similar auditory conversion means 130 converts the sound to a frequency and converts the frequency to a physical stimulus corresponding to a similar auditory sense, and a similar auditory learning step S140 at which a similar auditory learning means 140 trains a hearing impaired person to learn an emotion corresponding to the similar auditory sense, and thus, a particular frequency of a sound is stored as a frequency in an emotion a normal person feels and is converted to a physical stimulus, and each physical stimulus matched with a corresponding emotion inducing sound is transformed into data for the use of the data in the training of hearing impaired people to accurately feel emotions in response to physical stimuli converted from sounds.

Also, Prior Art 2 Korean Patent Publication No. 2003-0029660 (Apr. 16, 2003) relates to an apparatus and method for prenatal care using fetal emotion recognition. Prior Art 2 includes a fetal emotion recognition unit for recognizing an emotional state of a child in response to a bio-signal generated from the child, a mother emotion recognition unit for recognizing an emotional state of a mother in response to a bio-signal generated from the mother, a surrounding environment monitoring unit for generating an environmental friendliness level value corresponding to a numerical measure of the influence of a surrounding environment on the child in response to visual, auditory, and air conditioning data of the surrounding environment in which the mother is disposed, and a fetal emotion control unit for analyzing the emotional state of the child in response to the emotional state of the child, the emotional state of the mother and the environmental friendliness level value, and generating a prenatal caring signal and an environment control signal for maintaining the child in emotionally stable state based on a result of the analysis, thereby recognizing the emotional states of the child and the mother through analysis of the bio-signals generated from the child and the mother. Also, taking the recognized emotional states of the child and the method and the influence of the surrounding environment in which the child is disposed into consideration together, analysis of the emotional state of the child and generation of the stimulus signals is continuously performed to maintain the child in emotionally stable state. Accordingly, it allows prenatal care based on fetal emotion recognition extracted by an objective method.

DISCLOSURE

Technical Problem

To solve the above mentioned problem of the related art, the present disclosure is directed to providing a system and method for inspecting an emotion recognition capability using multisensory information that inspects the ability of discerning emotional states of others by using multisensory information representing others' emotions.

Further, to solve the above mentioned problem of the related art, the present disclosure is directed to providing a system and method for training emotion recognition using multisensory information that may improve the ability of a user to recognize emotional states of others through iterative training after find out how well the user is able to recognize emotional states of others.

Technical Solution

To achieve the above object, a system for inspecting an emotion recognition capability using multisensory information according to an embodiment of the present disclosure includes an output unit to output multisensory information made up of at least one emotional state of a subject to outside, an input unit to receive an input of emotional state information from a test person, the emotional state information indicating whether the at least one emotional state of the subject is the same based on the outputted multisensory information, a comparison identification unit to determine whether the inputted emotional state information is identical to reference emotional state information corresponding to the multisensory information pre-stored in a storage unit, and a control unit to judge an emotion recognition capability of the test person based on a result of determining the inputted emotional state information.

Particularly, the multisensory information may include information made up of a combination of visual information showing the subject and auditory information representing a voice of the subject.

To achieve the above object, a system for training emotion recognition using multisensory information according to another embodiment of the present disclosure includes an output unit to output multisensory information made up of at least one emotional state of a subject, an input unit to receive an input of emotional state information from a test person, the emotional state information indicating whether the at least one emotional state of the subject is the same based on the outputted multisensory information, a comparison identification unit to determine whether the inputted emotional state information is identical to reference emotional state information corresponding to the multisensory information pre-stored in a storage unit, and a control unit to judge an emotion recognition capability of the test person based on a result of determining the inputted emotional state information, and generate an output control signal to output multisensory information having a change in the difficulty level of emotional state combination based on a result of the judgment and transmit the output control signal to the output unit, wherein the output unit re-outputs multisensory information having a change in the difficulty level of emotional state combination based on the result of judging the emotion recognition capability in response to the output control signal, and the control unit compares the result of judging the emotion recognition capability of the test person to a result of judging an average emotion recognition capability to determine whether the emotion recognition capability of the test person is improved.

More preferably, the control unit may further include a difficulty level change module to change a difficulty level of emotional state combination of the multisensory information based on the result of judging the emotion recognition capability of the test person, an order change module to change an output order of the multisensory information based on the result of judging the emotion recognition capability of the test person, and a transmission module to generate an output control signal indicating a result of changing the difficulty level of emotional state combination or the output order of the multisensory information, and transmit the output control signal to the output unit.

Particularly, the multisensory information may include information made up of a combination of visual information showing the subject and auditory information representing a voice of the subject.

To achieve the above object, a method for inspecting an emotion recognition capability using multisensory information according to another embodiment of the present disclosure includes outputting, by an output unit, multisensory information made up of at least one emotional state of a subject to outside, receiving, by an input unit, an input of emotional state information from a test person, the emotional state information indicating whether the at least one emotional state of the subject is the same based on the outputted multisensory information, determining, by a comparison identification unit, whether the inputted emotional state information is identical to reference emotional state information corresponding to the multisensory information pre-stored in a storage unit, and judging, by a control unit, an emotion recognition capability of the test person based on a result of determining the inputted emotional state information.

Particularly, the outputting of multisensory information by the output unit may include outputting multisensory information made up of a combination of visual information showing the subject and auditory information representing a voice of the subject.

To achieve the above object, a method for training emotion recognition using multisensory information according to another embodiment of the present disclosure includes outputting, by an output unit, multisensory information made up of at least one emotional state of a subject, receiving, by an input unit, an input of emotional state information from a test person, the emotional state information indicating whether the at least one emotional state of the subject is the same based on the outputted multisensory information, determining, by a comparison identification unit, whether the inputted emotional state information is identical to reference emotional state information corresponding to the multisensory information pre-stored in a storage unit, judging, by a control unit, an emotion recognition capability of the test person based on a result of determining the emotional state information, generating, by the control unit, an output control signal to output multisensory information having a change in difficult level of emotional state combination corresponding to a result of judging the emotion recognition capability of the test person, and transmitting the generated output control signal to the output unit, re-outputting, by the output unit, multisensory information having a change in difficulty level of emotional state combination based on the received output control signal, receiving, by the input unit, an input of emotional state information of the subject from the test person based on the re-outputted multisensory information, re-determining, by the comparison identification unit, whether the inputted emotional state information is identical to pre-stored reference emotional state information corresponding to the multisensory information, and comparing, by the control unit, the result of judging the emotion recognition capability of the test person to a result of judging an average emotion recognition capability pre-stored in the storage unit based on a result of re-determining the emotional state information, to determine whether the emotion recognition capability of the test person is improved.

Particularly, the generating and transmitting of an output control signal to the output unit by the control unit may include generating, by the control unit, an output control signal indicating a result of changing the difficulty level of emotional state to combination of the multisensory information or an output order of the multisensory information based on a result of judging the emotion recognition capability of the test person, and transmitting the output control signal to the output unit.

Advantageous Effects

The system and method for inspecting an emotion recognition capability using multisensory information and the system and method for training emotion recognition using multisensory information according to the present disclosure has an effect on easy ascertainment of a test person's ability to recognize emotions of others by discerning emotional states of others using multisensory information.

Also, the system and method for inspecting an emotion recognition capability using multisensory information and the system and method for training emotion recognition using multisensory information according to the present disclosure has an effect on improvement in a test person's emotion recognition ability through iterative ascertainment of the emotion recognition ability at varying difficulty levels of emotional state combination of multisensory information after ascertaining the test person's current ability to recognize emotions of others.

Further, the system and method for inspecting an emotion recognition capability using multisensory information and the system and method for training emotion recognition using multisensory information according to the present disclosure has an effect on objective ascertainment of emotion recognition abilities in patients suffering from schizophrenia, autism, and depression although they look normal.

Along with this, the system and method for inspecting an emotion recognition capability using multisensory information and a system and method for training emotion recognition using multisensory information according to the present disclosure has an effect on improvement of emotion recognition abilities in patients suffering from schizophrenia, autism, and depression through iterative training at varying difficulty levels of multisensory information.

DESCRIPTION OF DRAWING

FIG. 4 is a table showing reference emotional state information for each combination of multisensory information.

BEST MODE

Hereinafter, the present disclosure will be described in sufficient detail for those skilled in the art to easily carry out it with reference to the preferred embodiments and accompanying drawings. However, the present disclosure may be embodied in a variety of different forms, and is not limited to the disclosed embodiments.

Figure 1:
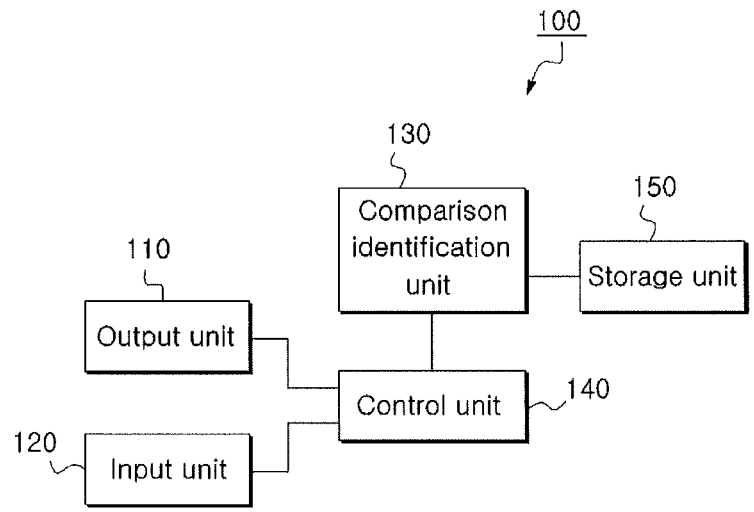
FIG. 1 is a block diagram of a system for inspecting an emotion recognition capability using multisensory information according to an embodiment of the present disclosure.

FIG. 1 is a block diagram of a system for inspecting an emotion recognition capability using multisensory information according to an embodiment of the present disclosure.

As shown in FIG. 1, the system 100 for inspecting an emotion recognition capability using multisensory information according to the present disclosure includes an output unit 110, an input unit 120, a comparison identification unit 130, a control unit 140, and a storage unit 150, and may be implemented through a computer input/output device and a processor.

The output unit 110 outputs multisensory information made up of at least one emotional state of a subject to outside, and may be implemented in the form of a monitor and a speaker. Particularly, the multisensory information is information including a combination of visual information showing the subject reacting to a variety of stimuli and auditory information representing a voice of the subject.

For example, where a stimulus of a pleasant music is given, the subject makes a joyful and happy expression, and the output unit 110 outputs multisensory information made up of a combination of visual information obtained by photographing the subject at the moment and auditory information representing a pleasant voice of the subject at the moment. Alternative, the output unit 110 may select visual information obtained by photographing the subject and auditory information of the subject and output only one of the information, to find out how well the test person is able to recognize emotions of others.

The input unit 120 receives, from the test person, an input of emotional state information indicating whether a plurality of emotional states of the subject is the same based on the multisensory information representing a current emotional state of the subject outputted through the output unit 110.

For example, when multisensory information including visual information showing that the subject is smiling and auditory information representing a laughing voice of the subject is outputted through the output unit, a current emotional state of the subject is found the same based on the visual information and the auditory information of the multisensory information, and emotional state information found the same is inputted from the test person to the input unit 120.

The comparison identification unit 130 determines whether the inputted emotional state information is identical to reference emotional state information corresponding to the multisensory information pre-stored in the storage unit.

For example, if the emotional state information inputted from the test person through the input unit 120 is a joyful state and the reference emotional state information corresponding to the multisensory information outputted through the output unit 110 is a joyful state, the comparison identification unit may determine that the inputted emotional state information is identical to the reference emotional state information.

The control unit 140 judges an emotion recognition capability of the test person based on a result of determining the inputted emotional state information. For example, the control unit may judge that the ability of the test person to recognize emotions of others is good based on a result of determining that the inputted emotional state information is identical to the reference emotional state information.

The storage unit 150 pre-stores a plurality of multisensory information to output through the output unit 110 and reference emotional state information corresponding to the plurality of multisensory information.

Hereinafter, a detailed description of a system for training emotion recognition using multisensory information according to the present disclosure is provided with reference to FIG. 2.

Figure 2:
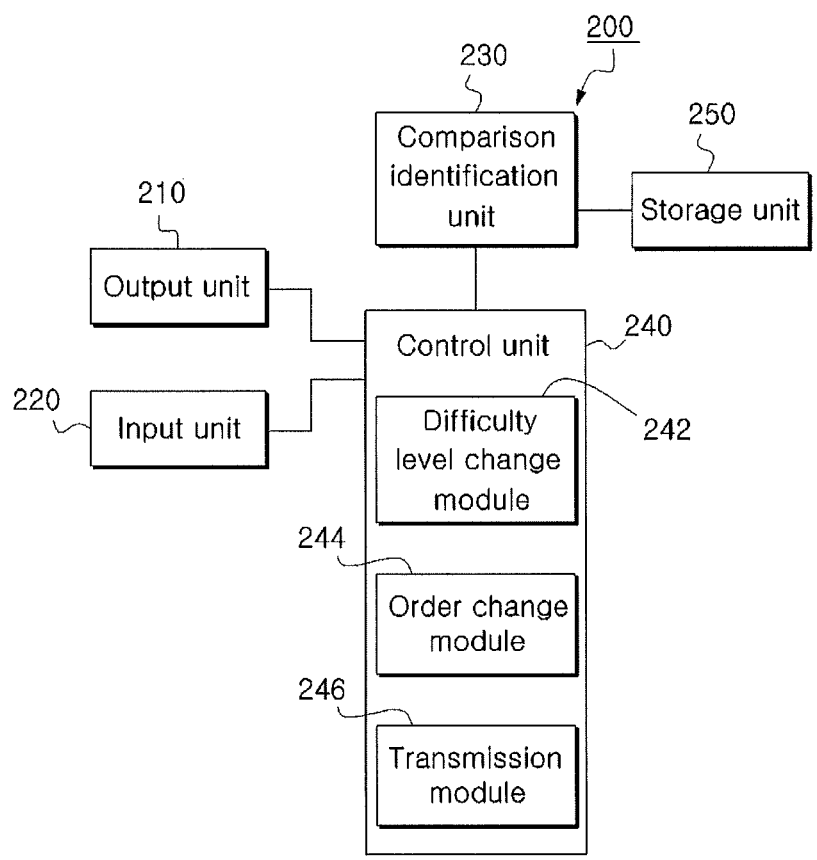
FIG. 2 is a block diagram of a system for training emotion recognition using multisensory information according to another embodiment of the present disclosure.

FIG. 2 is a block diagram of a system for training emotion recognition using multisensory information according to another embodiment of the present disclosure.

As shown in FIG. 2, the system 200 for training emotion recognition using multisensory information according to the present disclosure includes an output unit 210, an input unit 220, a comparison identification unit 230, a control unit 240, and a storage unit 250, and may be implemented through a computer input/output device and a processor.

The output unit 210 outputs multisensory information made up of a combination of a plurality of emotional states of a subject. In this instance, the multisensory information refers to information including a combination of visual information showing the subject and auditory information representing a voice of the subject. The output unit 210 re-outputs multisensory information having a change in difficulty level of emotional state combination based on a result of judging the emotion recognition capability in response to the output control signal.

The input unit 220 receives, from a test person, an input of emotional state information indicating whether at least one emotional state of the subject is the same based on the outputted multisensory information.

The comparison identification unit 230 determines whether the inputted emotional state information is identical to reference emotional state information corresponding to the multisensory information pre-stored in the storage unit 250.

The control unit 240 judges an emotion recognition capability of the test person based on a result of determining the inputted emotional state information, and generates an output control signal to output multisensory information having a change in difficult level of emotional state combination based on a result of the judgment and transmits the output control signal to the output unit. The control unit 240 compares a result of judging the emotion recognition capability of the test person to a result of judging an average emotion recognition capability, and determines whether the emotion recognition capability of the test person is improved.

The control unit 240 includes a difficulty level change module 242, an order change module 244, and a transmission module 246.

The difficulty level change module 242 changes a difficulty level of emotional state combination of the multisensory information based on the result of judging the emotion recognition capability of the test person.

The order change module 244 changes an output order of the multisensory information based on the result of judging the emotion recognition capability of the test person.

The transmission module 246 generates an output control signal indicating a result of changing the difficulty level of emotional state combination or an output order of the multisensory information, and transmits the output control signal to the output unit 210.

The storage unit 250 pre-stores a plurality of multisensory information to output through the output unit 210, reference emotional state information corresponding to the multisensory information, and a result of judging the average emotion recognition capability.

Hereinafter, a description of a method for inspecting an emotion recognition capability using multisensory information according to another embodiment of the present disclosure is provided with reference to FIG. 3.

Figure 3:
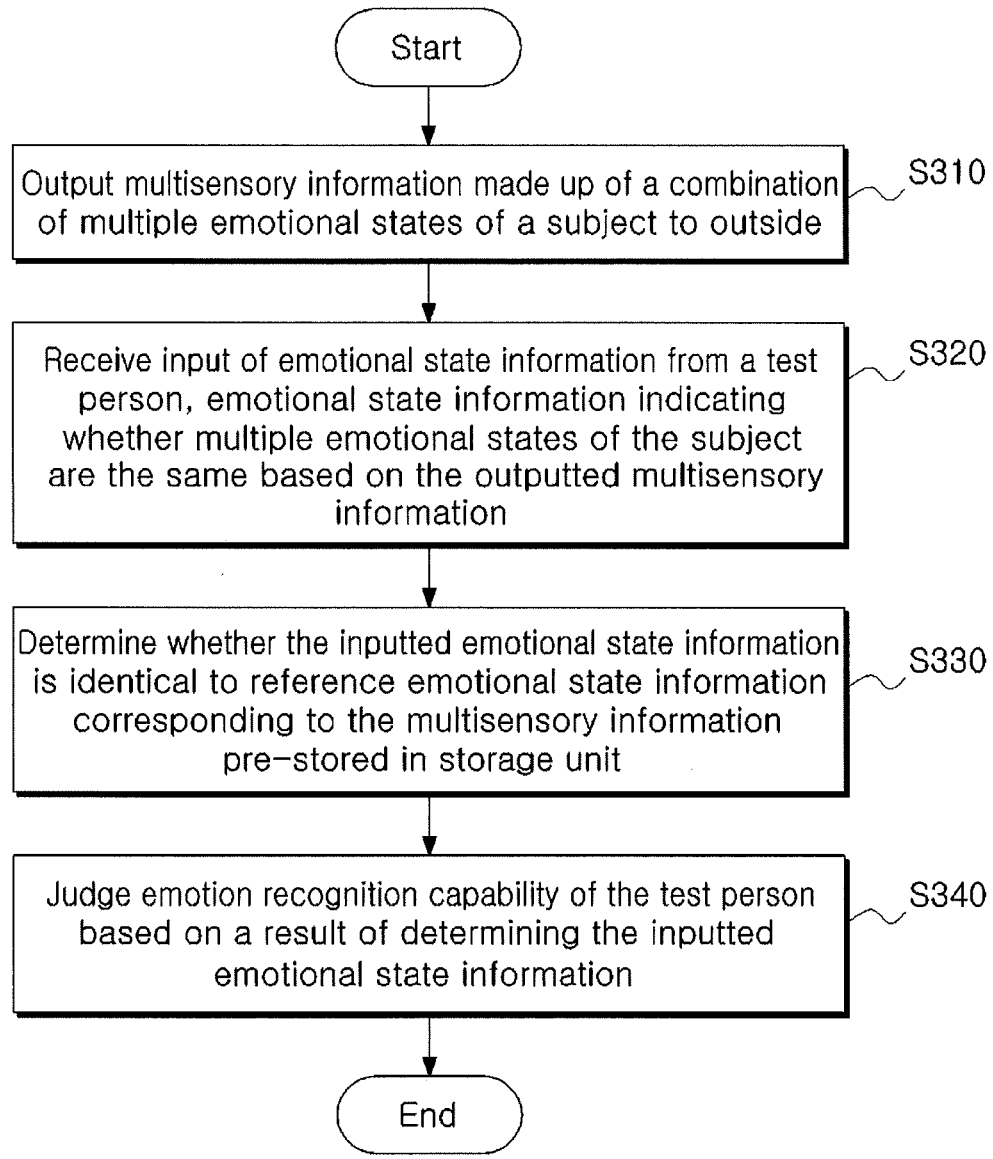
FIG. 3 is a flowchart of a method for inspecting an emotion recognition capability using multisensory information according to still another embodiment of the present disclosure.

FIG. 3 is a flowchart of a method for inspecting an emotion recognition capability using multisensory information according to still another embodiment of the present disclosure.

As shown in FIG. 3, in the method for inspecting an emotion recognition capability using multisensory information according to the present disclosure, an output unit outputs multisensory information made up of at least one emotional state of a subject to outside (S310). In this instance, the multisensory information being outputted refers to information including a combination of visual information showing the subject reacting to a variety of stimuli and auditory information representing a voice of the subject.

That is, where a stimulus of a pleasant music is given, the subject makes a joyful and happy expression, and the output unit 110 outputs multisensory information made up of a combination of visual information obtained by photographing the subject at the moment and auditory information representing a laughing voice of the subject at the moment.

In response, an input unit receives, from a test person, an input of emotional state information indicating whether a plurality of emotional states of the subject is the same based on the outputted multisensory information (S320).

For example, as shown in FIG. 4, where the multisensory information outputted through the output unit includes visual information representing happiness of the subject and auditory information representing happiness of the subject, the test person determines that the subject is happy by both the visual information and the auditory information, and the input unit receives an input of emotional state information indicating that the visual information and the auditory information of the multisensory information is the same.

Subsequently, a comparison identification unit determines whether the inputted emotional state information is identical to reference emotional state information corresponding to the multisensory information pre-stored in a storage unit (S330). That is, for multisensory information made up of a combination of visual information showing a smiling face of the subject and auditory information representing a laughing voice, it is identical to reference emotional state information, and the multisensory information and the corresponding reference emotional state information is stored in the storage unit.

For example, when the emotional state information inputted through the input unit is the same and the reference emotional state information corresponding to the multisensory information previously outputted through the output unit is the same, the comparison identification unit may determine that the inputted emotional state information is identical to the reference emotional state information.

Then, a control unit judges an emotion recognition capability of the test person based on a result of determining the inputted emotional state information (S340). For example, when the emotional state information is found identical as a result of the determination by the comparison identification unit, the control unit may determine that the emotion recognition capability of the test person is good. However, on the contrary, when the emotional state information is not identical as a result of the determination by the comparison identification unit, the control unit may determine that the test person is deficient in the ability to recognize emotions of others.

As described in the foregoing, the test person may predict an emotional state of the subject through the multisensory information representing the emotional state of the subject, and how well the test person is able to recognize emotions of others may be figured out by verifying whether the predicted emotional state is correct. In this instance, it is possible to score the emotion recognition capability of the test person.

Accordingly, after testing the emotion recognition capability of the test person, when the test person is found deficient in the ability to recognize emotions of others, a training method for improving the emotion recognition capability of the test person may be studied.

Hereinafter, a description of a method for training emotion recognition using multisensory information according to another embodiment of the present disclosure is provided with reference to FIG. 5.

Figure 5:
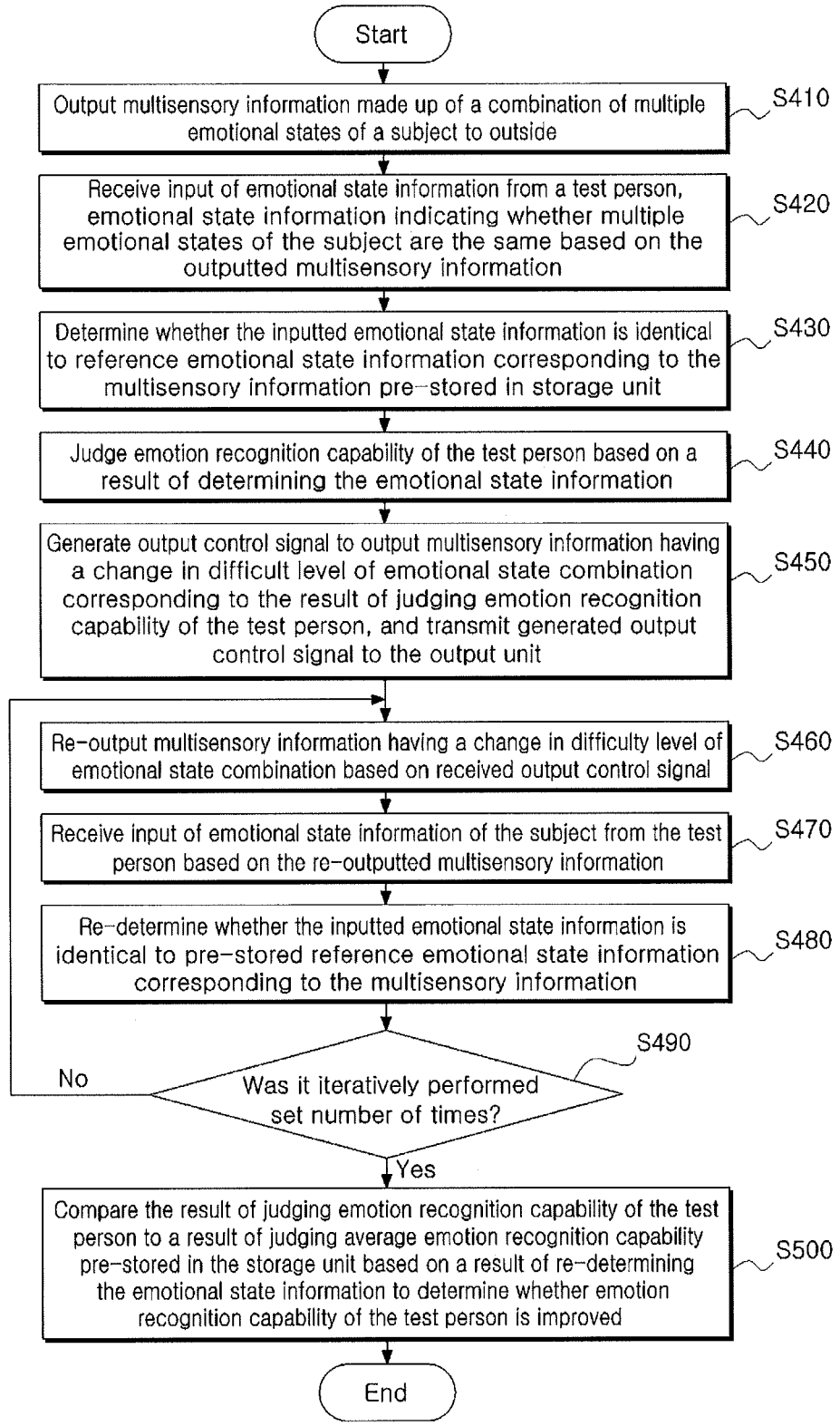
FIG. 5 is a flowchart of a method for training emotion recognition using multisensory information according to yet another embodiment of the present disclosure.

FIG. 5 is a flowchart of a method for training emotion recognition using multisensory information according to yet another embodiment of the present disclosure.

As shown in FIG. 5, according to the method, an input unit first receives an input of a score produced by numerically calculating an emotion recognition capability of a test person on standard score.

Subsequently, an output unit outputs multisensory information made up of a combination of a plurality of emotional state information of a subject to have a preset difficulty level corresponding to the inputted score (S410). In this instance, the difficulty level of emotional state combination of the multisensory information may be determined based on the standard score indicating the emotion recognition capability of the test person.

For example, when assuming the difficulty level of combination of the multisensory information is set such that it is divided into a total of five levels, the first level corresponds to a face having a lowest difficulty level of combination in which one of the two emotional state information is prominent, and with the movement towards higher levels, two emotional state information is combined at a similar ratio without any prominent emotional state.

For example, the first level is used when the standard score indicating the emotion recognition capability of the test person is less than or equal to −2, and −91 to 100% of a particular emotion is present. For example, a happy face is a composite for happiness and anger at a ratio of 95:5, and an angry face is a composite for anger and happiness at a ratio of 95:5.

The second level is used when the standard score indicating the emotion recognition capability of the test person is higher than or equal to −2 and less than —1, and 81 to 90% of a particular emotion is present. For example, a happy face is a composite for happiness and anger at a ratio of 85:15, and an angry face is a composite for anger and happiness at a ratio of 85:15.

The third level is used when the standard score indicating the emotion recognition capability of the test person is higher than or equal to −1 and less than 0, and 71 to 80% of a particular emotion is present. For example, a happy face is a composite for happiness and anger at a ratio of 75:25, and an angry face is a composite for anger and happiness at a ratio of 75:25.

The fourth level is used when the standard score indicating the emotion recognition capability of the test person is higher than or equal to 0 and less than 1.5, and 61 to 70% of a particular emotion is present. For example, a happy face is a composite for happiness and anger at a ratio of 65:35, and an angry face is a composite for anger and happiness at a ratio of 65:35.

The fifth level is used when the standard score indicating the emotion recognition capability of the test person is higher than or equal to 1.5, and 51 to 60% of a particular emotion is present. For example, a happy face is a composite for happiness and anger at a ratio of 55:45, and an angry face is a composite for anger and happiness at a ratio of 55:45.

An input unit receives, from the test person, emotional state information indicating whether the plurality of emotional states of the subject is the same based on the outputted multisensory information (S420).

A comparison identification unit determines whether the inputted emotional state information is identical to reference emotional state information corresponding to the multisensory information pre-stored in a storage unit (S430).

A control unit judges an emotion recognition capability of the test person based on a result of determining the emotional state information (S440).

The control unit generates an output control signal to output multisensory information having a change in difficulty level of emotional state combination, corresponding to a result of judging the emotion recognition capability of the test person, and transmits the generated output control signal to the output unit (S450). In this instance, the control unit may generate an output control signal indicating a result of changing the difficulty level of emotional state combination of the multisensory information or an output order of the multisensory information based on the result of judging the emotion recognition capability of the test person, and transmit the output control signal to the output unit.

Figure 6:
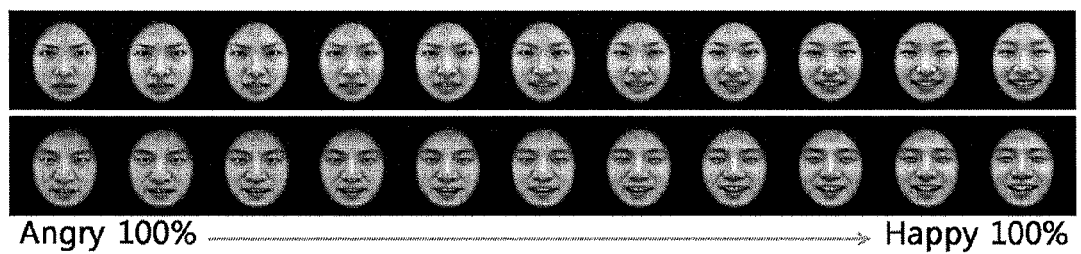
FIG. 6 is a diagram showing multisensory information for each difficulty level of emotions.

FIG. 6 is a diagram showing multisensory information for each difficulty level of emotions.

For example, an emotional state may be set such that it is divided into a plurality of levels from happy 100% to angry 100%, and stored in a storage unit.

Particularly, when a test person is found deficient in the emotion recognition capability, the difficulty level of emotional state combination of multisensory information is changed to a lower level to generate an output control signal for selecting multisensory information corresponding to happy 100% or angry 100%.

Alternatively, on the contrary, when an emotion recognition capability of a test person is found to be good, the difficulty level of emotional state combination of multisensory information is changed to a higher level to output an output control signal for selecting multisensory information corresponding to happy 50% or angry 50%, not the extreme of happy 100% or angry 100%.

The output unit re-outputs multisensory information having a change in difficulty level of emotional state combination based on the received output control signal (S460).

The input unit receives an input of emotional state information of the subject from the test person based on the re-outputted multisensory information (S470). In this instance, when the input unit receives an input of emotional state information from the test person based on the outputted multisensory information, an input time limit may be set, and the input time limit may be set to decrease or increase with the change in difficulty level of emotional state combination.

The comparison identification unit re-determines whether the inputted emotional state information is identical to pre-stored reference emotional state information corresponding to the multisensory information (S480).

Subsequently, the control unit determines whether the output and input of the multisensory information was iteratively performed a preset number of times (S490). In this instance, the set number of times refers to the number of repetitions of training, and may be changed and set by selection of the test person.

Accordingly, when the output and input of the multisensory information is iteratively performed the preset number of times, the control unit compares a result of judging an emotion recognition capability of the test person to a result of judging an average emotion recognition capability pre-stored in the storage unit based on a result of re-determining the emotional state information, to determine whether the emotion recognition capability of the test person is improved (S500).

Figure 7:
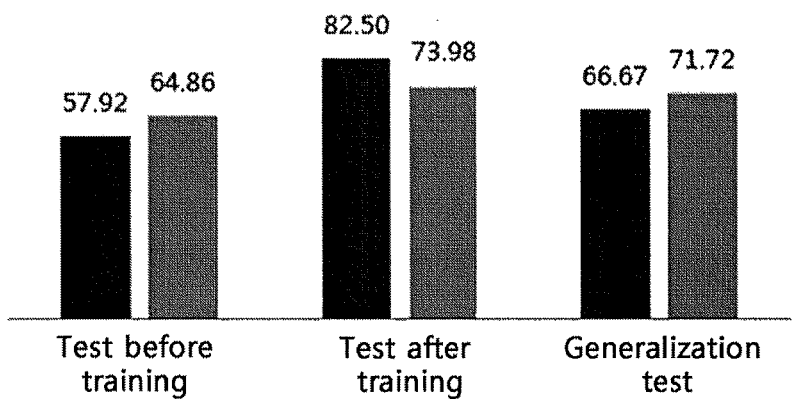
FIG. 7 is a graph showing an emotion recognition capability of a test person after emotion recognition training.
Figure 7:
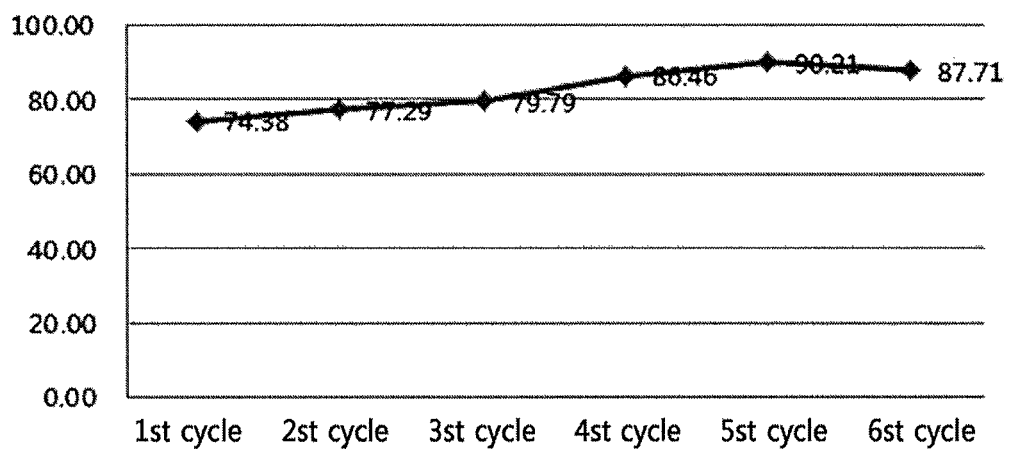

FIG. 7 is a graph showing the emotion recognition capability of the test person after emotion recognition training.

For example, as shown in FIG. 7(a), if a result of judging the emotion recognition capability of the test person is 82.50 and a result of judging the average emotion recognition capability pre-stored in the storage unit is 73.98, it is determined that the emotion recognition capability of the test person was improved.

Also, the result of judging the emotion recognition capability of the test person may change over number of training cycles.

As shown in FIG. 7(b), it can be seen that the result of judging the emotion recognition capability during the first training cycle is 74.38, while the result of judging the emotion recognition capability during the fifth training cycle is 90.21, and it can be seen that the emotion recognition capability is improved with the increasing number of training.

Also, as described above, after training the emotion recognition capability of the test person multiple times, it is possible to verify whether the emotion recognition capability was improved through a generalization test.

The generalization test for the emotion recognition capability uses visual information showing other subject or auditory information representing a voice of other subject, not multisensory information of the same type used in emotion recognition training.

To this end, the generalization test requires an input unit to receive an input of information associated with at least one of a gender, an age, and a human race of a subject, and an input of a voice tone of the subject or content information from a test person. For example, to see the ability to recognize an emotion of a woman in her twenties, the input unit may receive an input of 'twenties' and 'woman' and an input of a 'very high tone' of voice and a content of 'let's go eating' from the test person.

Subsequently, an output unit outputs multisensory information including a combination of visual information and auditory information corresponding to the information associated with at least one of gender, age, and human race of the subject, the voice tone of the subject or the content information inputted through the input unit.

Subsequently, the input unit receives, from the test person, an input of emotional state information indicating whether a plurality of emotional states of the subject is the same based on the outputted multisensory information.

Subsequently, a comparison identification unit determines whether the inputted emotional state information is identical to reference emotional state information corresponding to the multisensory information pre-stored in a storage unit.

Then, a control unit may judge the emotion recognition capability of the test person generalized based on a result of determining the emotional state information.

Also, the system and method for inspecting an emotion recognition capability using multisensory information and the system and method for training emotion recognition using multisensory information may be stored in a computer-readable recording medium having recorded thereon a program for causing a computer to execute. In this instance, the computer-readable recording medium includes any type of recording device in which data readable by a computer system is stored. Examples of the computer-readable recording medium include ROM, RAM, CD-ROM, DVD±ROM, DVD-RAM, a magnetic tape, a floppy disk, a hard disk, and an optical data storage device. Also, the computer-readable recording medium may be distributed over network-coupled computer systems so that a computer-readable code is stored and executed in a distributed fashion.

The system and method for inspecting an emotion recognition capability using multisensory information and the system and method for training emotion recognition using multisensory information according to the present disclosure has an effect on easy ascertainment of the ability to recognize emotions of others by discerning an emotional state of a subject using multisensory information.

Also, the system and method for inspecting an emotion recognition capability using multisensory information and the system and method for training emotion recognition using multisensory information according to the present disclosure has an effect on improvement in a user's emotion recognition ability through iterative training of the recognition ability at varying difficulty levels of multisensory information after ascertaining the ability to recognize emotions of others.

Further, the system and method for inspecting an emotion recognition capability using multisensory information and the system and method for training emotion recognition using multisensory information according to the present disclosure has an effect on easy recognition of emotional states of others by patients suffering from schizophrenia, autism, and depression, thereby facilitating improvement in emotion recognition ability of a user with the change in difficulty level of multisensory information after ascertaining the user's current ability to recognize emotions.

While the preferred embodiments of the present disclosure have been hereinabove described, the present disclosure is not limited thereto, and it should be noted that various modifications may be made to the present disclosure within the spirit and scope of the present disclosure and such modifications fall within the appended claims.

The invention claimed is:

1. A system for training emotion recognition using multisensory information, comprising:
   an output unit to output multisensory information made up of at least one emotional state of a subject;
   an input unit to receive an input of emotional state information from a test person, the emotional state information indicating whether the at least one emotional state of the subject is the same based on the outputted multisensory information;
   a comparison identification unit to determine whether the inputted emotional state information is identical to reference emotional state information corresponding to the multisensory information pre-stored in a storage unit; and
   a control unit to judge an emotion recognition capability of the test person based on a result of determining the inputted emotional state information, and generate an output control signal to output multisensory information having a change in difficulty level of emotional state combination based on a result of the judgment and transmit the output control signal to the output unit,
   wherein difficulty level of emotional state combination is adjusted according to composite ratio of composed emotions when multisensory information is made up of a combination of a plurality of emotional state information,
   the output unit re-outputs multisensory information having a change in difficulty level of emotional state combination based on the result of judging the emotion recognition capability in response to the output control signal, and the control unit compares the result of judging the emotion recognition capability of the test person to a result of judging an average emotion recognition capability to determine whether the emotion recognition capability of the test person is improved.

2. The system for training emotion recognition using multisensory information according to claim 1, wherein the control unit further comprises:
- a difficulty level change module to change a difficulty level of emotional state combination of the multisensory information based on the result of judging the emotion recognition capability of the test person;
- an order change module to change an output order of the multisensory information based on the result of judging the emotion recognition capability of the test person; and
- a transmission module to generate an output control signal indicating a result of changing the difficulty level of emotional state combination or the output order of the multisensory information, and transmit the output control signal to the output unit.

3. The system for training emotion recognition using multisensory information according to claim 1, wherein the multisensory information is information made up of a combination of visual information showing the subject and auditory information representing a voice of the subject.

4. A method for training emotion recognition using multisensory information, comprising:
- outputting, by an output unit, multisensory information made up of at least one emotional state of a subject;
- receiving, by an input unit, an input of emotional state information from a test person, the emotional state information indicating whether the at least one emotional state of the subject is the same based on the outputted multisensory information;
- determining, by a comparison identification unit, whether the inputted emotional state information is identical to reference emotional state information corresponding to the multisensory information pre-stored in a storage unit;
- judging, by a control unit, an emotion recognition capability of the test person based on a result of determining the emotional state information;
- generating, by the control unit, an output control signal to output multisensory information having a change in difficult level of emotional state combination corresponding to a result of judging the emotion recognition capability of the test person, and transmitting the generated output control signal to the output unit;
- re-outputting, by the output unit, multisensory information having a change in difficulty level of emotional state combination based on the received output control signal;
- receiving, by the input unit, an input of emotional state information of the subject from the test person based on the re-outputted multisensory information;
- re-determining, by the comparison identification unit, whether the inputted emotional state information is identical to pre-stored reference emotional state information corresponding to the multisensory information; and
- comparing, by the control unit, the result of judging the emotion recognition capability of the test person to a result of judging an average emotion recognition capability pre-stored in the storage unit based on a result of re-determining the emotional state information, to determine whether the emotion recognition capability of the test person is improved.

5. The method for training emotion recognition using multisensory information according to claim 4, wherein the generating and transmitting of an output control signal to the output unit by the control unit comprises generating, by the control unit, an output control signal indicating a result of changing the difficulty level of emotional state combination of the multisensory information or an output order of the multisensory information based on a result of judging the emotion recognition capability of the test person, and transmitting the output control signal to the output unit.

6. The system according to claim 1, wherein the output unit is configured to provide visual and/or auditory information.

7. The system according to claim 6, wherein the output unit comprises a monitor or speaker.

8. The system according to claim 1, wherein the input unit is configured to receive visual and/or auditory information.

9. The system according to claim 8, wherein the input unit comprises a camera or microphone.

10. The system according to claim 1, wherein the storage unit comprises a computer-readable recording medium.

11. The system according to claim 10, wherein the computer-readable recording medium is ROM, RAM, CD-ROM, DVD±ROM, DVD-RAM, a magnetic tape, a floppy disk, a hard disk, or an optical data storage device.

* * * * *